United States Patent [19]

Delarge et al.

[11] 4,055,650

[45] Oct. 25, 1977

[54] CERTAIN 4-PHENOXY(OR PHENYLTHIO)-3-N-ACYLATED-SULFONAMIDO-PYRIDINES

[75] Inventors: Jacques E. Delarge, Dolembreux; Charles L. Lapiere, Tongeren; Andre H. Georges, Ottignies, all of Belgium

[73] Assignee: A. Christiaens Societe Anonyme, Brussels, Belgium

[21] Appl. No.: 694,421

[22] Filed: June 9, 1976

Related U.S. Application Data

[63] Continuation-in-part of Ser. No. 568,759, April 16, 1975, Pat. No. 4,018,929.

[30] Foreign Application Priority Data

Apr. 17, 1974 United Kingdom .............. 16836/74

[51] Int. Cl.$^2$ .................... C07D 213/71; A61K 31/44
[52] U.S. Cl. ............................. 424/263; 260/294.8 F; 260/294.8 G
[58] Field of Search ................. 260/294.8 F; 424/263

[56] References Cited

U.S. PATENT DOCUMENTS

| | | | |
|---|---|---|---|
| 3,674,794 | 7/1972 | Mizzoni et al. | 260/294.8 F |
| 3,819,639 | 6/1974 | DeLarge et al. | 260/294.8 F |
| 3,904,636 | 9/1975 | DeLarge et al. | 260/294.8 F |

*Primary Examiner*—Alan L. Rotman

*Attorney, Agent, or Firm*—Sughrue, Rothwell, Mion, Zinn and Macpeak

[57] ABSTRACT

This invention relates to new derivatives of pyridine having hypo-uricemic or hypolipemic properties.

The new derivatives of pyridine may be represented by the following general formula:

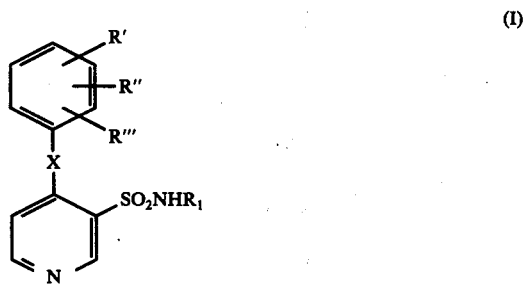

(I)

in which X represents an oxy or thio group, $R_1$ represents hydrogen, a group of the formula $R_3NHCO$ (II), wherein $R_3$ represents a $C_1$-$C_4$-alkyl, cycloalkyl or possibly substituted phenyl group, or a group of the formula $R_4$—CO (III) in which $R_4$ represents a $C_1$-$C_4$-alkyl group or a possibly substituted phenyl group, and R', R" and R'" represent each a possible substituent selected from the group comprising the halogens, the trifluoromethyl and the $C_1$-$C_4$ alkyl groups.

6 Claims, No Drawings

CERTAIN 4-PHENOXY(OR PHENYLTHIO)-3-N-ACYLATED-SULFONAMIDO-PYRIDINES

This application is a continuation-in-part application of Ser. No. 568,759, filed Apr. 16, 1975, now U.S. Pat. No. 4,018,929.

BRIEF DESCRIPTION OF THE INVENTION

This invention relates to new derivatives of pyridine, their preparation and use.

The new derivatives of pyridine are of the following formula:

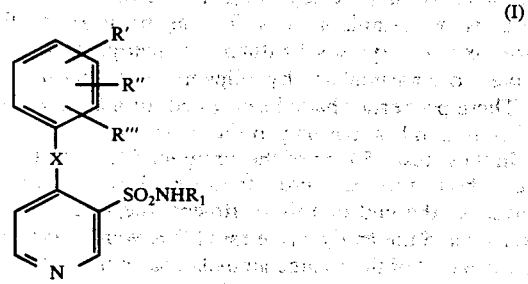
(I)

in which X represents an oxy or thio group; $R_1$ represents hydrogen or a group of the formula:

(II)

wherein $R_3$ represents a $C_1$-$C_4$ alkyl, cycloalkyl, unsubstituted phenyl or substituted phenyl group, or a group of the formula:

$$R_4CO \qquad (III)$$

wherein $R_4$ represents a $C_1$-$C_4$ alkyl group or a possibly substituted phenyl group; R', R" and R'" represent each hydrogen or a substituent selected from the group comprising the halogen atoms, the trifluoromethyl group and the $C_1$-$C_4$ alkyl groups.

The invention also relates to the N-oxides of the compounds of formula I in which the oxygen atom is attached to the nitrogen atom of the pyridine, and to the base and acid addition salts of said compounds.

DETAILED DESCRIPTION OF THE INVENTION

The compounds according to this invention, i.e. the compounds of formula I, may be prepared by various processes:

First Process

When it is desired to obtain a compound of formula I, wherein $R_1$ represents a $R_3NHCO$ group as defined above, a first process comprises reacting a compound of the following formula:

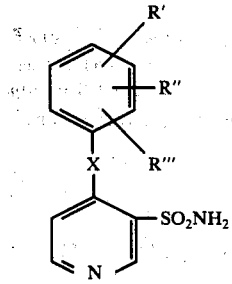
(IV)

in which X, R', R" and 4''' are as defined above, with an isocyanate of the formula:

$$R_3N = C = O \qquad (V)$$

in which $R_3$ has the above meanings.

Second Process

When it is desired to obtain a compound of formula I, wherein $R_1$ represents a $R_3NHCO$ group as defined above, another process comprises reacting a compound of formula IV with an alkylhaloformate of the formula:

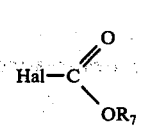
(VI)

in which $R_7$ represents a $C_1$-$C_4$-alkyl group and Hal represents an halogen atom, and an amine of the formula:

$$R_3NH_2 \qquad (VII)$$

in which $R_3$ has the above meanings.

Third Process

When it is desired to obtain a compound of formula I, wherein $R_1$ represents hydrogen, a $R_3NHCO$ group as above defined or a $R_4CO$ group as above defined, this process comprises reacting a compound of the formula:

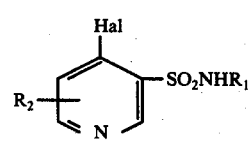
(VIII)

in which $R_1$ is as defined above, with a phenolate or thiophenolate of the formula:

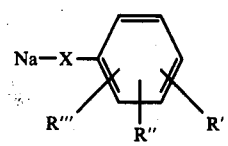
(IX)

in which X, R', R" and R'" are as defined above.

Fourth Process:

When it is desired to obtain a compound of formula I, wherein $R_1$ represents a $R_4CO$ group as defined above, this process comprises reacting a compound of formula IV with an anhydride of an alkane-carboxylic or arylcarboxylic acid of the formula:

$(R_4—CO)_2O$                                           (X)

or with a chloride of an alkane-carboxylic or arylcarboxylic acid of the formula:

$R_4COCl$                                                (XI)

Fifth Process

When it is desired to obtain a compound of formula I, in which $R_1$ represents $R_3NHCO$, a further process comprises heating a compound of formula I, in which $R_1$ represents a $R_3NHCS$ group, in an aqueous-alcoholic solution of sodium carbonate with an excess of HgO.

Sixth Process

When it is desired to obtain the N-oxides of the compounds of formula I, the above processes are applied, except that the corresponding N-oxides of the starting pyridine derivatives are used.

Seventh Process

When it is desired to obtain the N-oxides of the compounds of formula I, the process comprises treating a compound of formula I with meta-chloroperoxy-benzoic acid.

The compounds of formula IV, which are used as starting material in the first and second processes, may be prepared by the third above-described process, starting with a 4-halogeno-pyridine-sulfonamide.

The compounds of formula I in which $R_1$ represents $R_3NHCS$, which are used as starting materials in the fifth process, may be prepared by the first above-described process, using isothiocyanate instead of isocyanate.

It has been found that the compounds of formula I have hypo-uricemying or hypolipemying properties. Specifically, it has been found that the compounds of formula I, in which the phenoxy or thiophenoxy moiety is substituted by trifluorometyl or alkyl, have more particularly hypo-uricemying properties. The compounds of formula I in which the phenoxy or thiophenoxy moiety is substituted by halogens or nitro, have more particularly hypolipemying properties.

These properties have been tested for a large number of compounds according to the invention.

In these tests, 50 mg of the compound to be tested per kg of body weight, were administered to rats during 7 days. At the end of this treatment, the uric acid rate (URA) and the triglyceride rate (TG) were determined in the blood of the treated animals and compared to that of a group of reference animals.

The hypo-uricemying and hypolipemying activities are expressed as the percent decrease of the URA- or TG rate with respect to reference animals.

The results of the tests are given in the following tables.

TABLE I

| Compound | | | Formula I | | Percent decrease of URA rate |
|---|---|---|---|---|---|
| Code Nr | Example | X | $R_1$ | R', R'', R''' | |
| 553 | 21 | S | methylcarbamyl | 3-trifluoro-methyl | 37 |
| 554 | 22 | S | ethylcarbamyl | " | 18 |
| 555 | 23 | S | propylcarbamyl | " | 72 |
| 556 | 24 | S | isopropylcarbamyl | " | 80 |
| 529 | 9 | S | butylcarbamyl | " | 59 |
| 557 | 25 | S | tert.-butyl-carbamyl | " | 70 |
| 530 | 10 | S | cyclohexyl-carbamyl | " | 62 |
| 528 | 8 | S | hydrogen | " | 2 |
| 552 | 20 | S | acetyl | " | 57 |
| 532 | 12 | S | propionyl | " | 39 |
| 531 | 11 | S | parachlorobenzyl | " | 43 |
| 674 | 79 | S | methylcarbamyl | 4-methyl | 6 |
| 675 | 80 | S | ethylcarbamyl | " | 4 |
| 676 | 81 | S | propylcarbamyl | " | 5 |
| 677 | 82 | S | isopropylcarbamyl | " | 27 |
| 678 | 83 | S | butylcarbamyl | " | 23 |
| 671 | 76 | S | hydrogen | " | 4 |
| 672 | 77 | S | acetyl | " | 27 |

TABLE II

| Compound | | | Formula I | | Percent decrease of TG rate |
|---|---|---|---|---|---|
| Code Nr | Example | X | $R_1$ | R', R'', R''' | |
| 546 | 14 | S | methylcarbamyl | 3-chloro | 18 |
| 547 | 15 | S | ethylcarbamyl | " | 0 |
| 384 | 6 | S | propylcarbamyl | " | 22 |
| 548 | 16 | S | isopropylcarbamyl | " | 44 |
| 385 | 7 | S | tert.-butyl-carbamyl | " | 39 |
| 610 | 65 | S | phenylcarbamyl | " | 20 |
| 551 | 19 | S | parachloro-phenylcarbamyl | " | 43 |
| 549 | 17 | S | cyclohexyl- | " | 14 |

TABLE II-continued hypolipemying activity

| Compound | | | Formula I | | Percent decrease |
|---|---|---|---|---|---|
| Code Nr | Example | X | $R_1$ | R', R'', R''' | of TG rate |
| 560 | 28 | S | methylcarbamyl | 3,4-dichloro | 27 |
| 573 | 30 | S | ethylcarbamyl | " | 14 |
| 576 | 29 | S | propylcarbamyl | " | 31 |
| 574 | 31 | S | isopropylcarbamyl | " | 24 |
| 577 | 34 | S | butylcarbamyl | " | 16 |
| 575 | 32 | S | tert.-butylcarbamyl | " | 38 |
| 581 | 38 | S | methylcarbamyl | 3,5-dichloro | 38 |
| 582 | 39 | S | ethylcarbamyl | " | 38 |
| 583 | 40 | S | propylcarbamyl | " | 31 |
| 588 | 45 | S | isopropylcarbamyl | " | 45 |
| 589 | 46 | S | butylcarbamyl | " | 24 |
| 584 | 41 | S | tert.-butylcarbamyl | " | 37 |
| 585 | 42 | S | cyclohexylcarbamyl | " | 34 |
| 594 | 51 | S | methylcarbamyl | 2,6-dichloro | 32 |
| 595 | 52 | S | ethylcarbamyl | " | 44 |
| 596 | 53 | S | propylcarbamyl | " | 32 |
| 598 | 55 | S | butylcarbamyl | " | 16 |
| 599 | 56 | S | tert.-butylcarbamyl | " | 33 |
| 605 | 62 | S | propylcarbamyl | 2,6-dichloro-3-methyl | 5 |
| 606 | 63 | S | isopropylcarbamyl | " | 22 |
| 607 | 64 | S | butylcarbamyl | " | 21 |
| 361 | 2 | S | hydrogen | 3-chloro | 35 |
| 362 | 3 | S | acetyl | " | 18 |
| 545 | 13 | S | propionyl | " | 27 |
| 559 | 27 | S | acetyl | 3,4-dichloro | 30 |
| 561 | 29 | S | propionyl | " | 55 |
| 578 | 35 | S | parachlorobenzyl | " | 17 |
| 579 | 36 | S | hydrogen | 3,5-dichloro | 32 |
| 586 | 43 | S | acetyl | " | 50 |
| 580 | 37 | S | propionyl | " | 31 |
| 587 | 44 | S | parachlorobenzyl | " | 23 |
| 591 | 48 | S | hydrogen | 2,6-dichloro | 16 |
| 592 | 49 | S | acetyl | " | 40 |
| 593 | 50 | S | propionyl | " | 38 |
| 601 | 58 | S | hydrogen | 2,6-dichloro-3-methyl | 17 |
| 602 | 59 | S | acetyl | " | 18 |
| 603 | 60 | S | propionyl | " | 17 |
| 360 | 1 | O | hydrogen | 3-chloro | 19 |
| 365 | 5 | O | propylcarbamyl | " | 12 |

This invention relates therefore also to pharmaceutical compositions containing as active ingredient at least one compound of the formula I, or a N-oxide of such a compound of a base- or acid-addition salt thereof, together with a pharmaceutically acceptable vehicle or carrier.

The compounds of this invention may be administered in the form of dragees, tablets, capsules and suppositories at daily doses of 50 to 300 mg of active compund.

EXAMPLES

The following examples illustrate the preparation of compounds of formula I.

EXAMPLE 1

Preparation of 3-sulfonamido-4-(3'-chloro)-phenoxypyridine (formula I: R' = 3-chloro; $R_1$ = H and X = O).

Third process - A mixture of 3-sulfonamido-4-chloropyridine (0.02 mole), sodium meta-chlorophenolate (0.04 mole) and meta-chlorophenol (0.02 mole) is heated and maintained at about 160°–180° C during ½ hour. The mixture is taken up with 100 ml of alcohol, acidified by means of acetic acid and diluted with water. The desired product precipitates; m.p. 161°–163° C (white crystals).

EXAMPLE 2

Preparation of 3-sulfonamido-4-(3'-chloro)-thiophenoxypyridine (formula I: R' = 3-chlorophenyl; $R_1$ = H and X = S).

Third process—The following mixture is allowed to boil during 1 hour: 0.02 mole of 3-sulfonamido-4-chloropyridine and 0.03 mole of sodium methachlorothiophenolate. The mixture is diluted with an excess of water and acidified with acetic acid. The product crystallizes as white crystals; m.p. 150°–152° C.

EXAMPLE 3

Preparation of 3-acetylsulfonamido-4-(3-chloro)-thiophenoxypyridine (formula I: R' = 3-chloro; $R_1$ = $COCH_3$ and X = S).

A. Fourth Process 3-sulfonamido-4-(3'-chloro)-thiophenoxypyridine (5 g) is contacted with pyridine (25 ml) and acetic anhydride (25 ml) during 3 hours. The reacted mixture is poured into an excess of 10% NaOH, filtered if necessary and acidified by means of acetic acid. The product is separated, purified by dissolution in 200 ml of 5% $NaHCO_3$ in a mixture of water and alcohol (3:1) and again precipitated by means of acetic acid.

B. Third Process 3-acetylsulfonamido-4-chloropyridine (0.01 mole) and sodium metachlorothiophenolate (0.01 mole) and absolute ethanol (100 ml) are reflux heated during 1 hour. After distillation of 50 ml of ethanol, the mixture is diluted with an excess of water, giving a precipitate which is purified and isolated as in part A of this example. White product; m.p. 229°–230° C.

EXAMPLE 4

Preparation of
3-butylcarbamylsulfonamido-4-(3'-chloro)thiophenoxypyridine (formula I: R' = 3-chloro; $R_1$ = $CONHC_4H_9$ and X = S).

A. First process - 3-sulfonamido-4-(3'-chloro)thiophenoxypyridine (0.02 mole) is reacted with n-butylisocyanate (0.025 mole) in the presence of 1 to 2 ml of triethylamine by heating at 85°–95° C during 10 hours. The residue is taken up with alcohol (30 ml) and NaOH 2N, acidified by means of acetic acid and then diluted with an excess of water which gives a precipitate. The mixture is treated with a 5% solution of sodium bicarbonate in a mixture (3:1) of water and alcohol during 1 hour, then filtered and acidified, whereby the desired product precipitates.

B. The same product is also obtained by the third process using sodium metachlorothiophenolate and absolute ethanol as a diluent, in the manner described in example 1.

In both instances, one obtains a white product; m.p. 195°–197° C.

EXAMPLE 5

Preparation of
3-propylcarbamylsulfonamido-4-(3'-chloro)phenoxypyridine (formula I: R' = 3-chloro; $R_1$ = $CONHC_3H_7$ and X = O).

First process - 3-sulfonamido-4-(3'-chloro)phenoxypyridine (0.01 mole) is intimately mixed with propylisocyanate (0.0125 mole) and triethylamine (0.5 –1 ml). The mixture thus obtained is maintained 4 hours at 85°–95° C, taken up with 50 ml of alcohol and a few ml of NaOH 2N, heated to dissolve any soluble matter, acidified with acetic acid. 300 ml of water are then added thereto. The product is purified and isolated as described previously, using a solution of $NaHCO_3$ to give small white crystals; m.p. 177°–179° C.

EXAMPLES 6 to 84

Applying any of the above-described methods, the following compounds listed in the table hereinafter are prepared. Unless otherwise specified, all these products are white crystals, sparingly soluble in water, more soluble in alcohol and acetone, soluble in mineral acids and in bases: the acylsulfonamides and carbaminoylsulfonamides are soluble in hydroalcoholic solutions of $NaHCO_3$. The preferred recrystallization solvents are methanol, ethanol, ethanol-water and acetone-water mixtures, and sometimes ligroine.

| Example | Code Nr | X | $R_1$ | R', R", R''' | Melting point (° C) |
|---|---|---|---|---|---|
| 6 | 384 | S | propylcarbamyl | 3-chloro | 174–176 |
| 7 | 385 | S | tert.-butyl-carbamyl | " | 128 |
| 8 | 528 | S | hydrogen | 3-trifluoro-methylphenyl | 165 |
| 9 | 529 | S | butylcarbamyl | " | 167–168 |
| 10 | 530 | S | cyclohexyl-carbamyl | " | 183–185 |
| 11 | 531 | S | parachloro-benzoyl | " | 203–205 |
| 12 | 532 | S | propionyl | " | 169–171 |
| 13 | 545 | S | propionyl | 3-chloro | 229–230 |
| 14 | 546 | S | methylcarbamyl | " | 182 |
| 15 | 547 | S | ethylcarbamyl | " | 190 |
| 16 | 548 | S | isopropyl-carbamyl | " | 208 |
| 17 | 549 | S | phenylcarbamyl | " | 170 |
| 18 | 550 | S | parachloro-benzoyl | " | 223–225 |
| 19 | 551 | S | parachloro-phenylcarbamyl | " | 223 |
| 20 | 552 | S | acetyl | 3-trifluoro-methylphenyl | 190 |
| 21 | 553 | S | methylcarbamyl | " | 196 |
| 22 | 554 | S | ethylcarbamyl | " | 142 |
| 23 | 555 | S | propylcarbamyl | " | 156 |
| 24 | 556 | S | isopropyl-carbamyl | " | 165 |
| 25 | 557 | S | tert.-butyl-carbamyl | " | 180 |
| 26 | 558 | S | hydrogen | 3,4-dichloro | 166 |
| 27 | 559 | S | acetyl | " | 270 |
| 28 | 560 | S | methylcarbamyl | " | 227 |
| 29 | 561 | S | propionyl | " | 254 |
| 30 | 573 | S | ethylcarbamyl | " | 186–188 |
| 31 | 574 | S | isopropyl-carbamyl | " | 221 |
| 32 | 575 | S | tert.-butyl-carbamyl | " | 204–206 |
| 33 | 576 | S | propylcarbamyl | " | 207–209 |
| 34 | 577 | S | butylcarbamyl | " | 207 |
| 35 | 578 | S | parachloro-benzoyl | " | 275–276 |
| 36 | 579 | S | hydrogen | 3,5-dichloro | 206–208 |
| 37 | 580 | S | propionyl | " | 210 |
| 38 | 581 | S | methylcarbamyl | " | 214–216 |

-continued

| Example | Code Nr | X | R₁ | R', R", R''' | Melting point (° C) |
|---|---|---|---|---|---|
| 39 | 582 | S | ethylcarbamyl | " | 195–197 |
| 40 | 583 | S | propylcarbamyl | " | 207–209 |
| 41 | 584 | S | tert.-butyl-carbamyl | " | 156–158 |
| 42 | 585 | S | cyclohexylcarbamyl | " | 191–193 |
| 43 | 586 | S | acetyl | " | 225–227 |
| 44 | 587 | S | benzoyl | " | 268–270 |
| 45 | 588 | S | isopropyl-carbamyl | " | 198–200 |
| 46 | 589 | S | butylcarbamyl | " | 168–170 |
| 47 | 590 | S | phenylcarbamyl | 3,4-dichloro | 221 |
| 48 | 591 | S | hydrogen | 2,6-dichloro | 268 |
| 49 | 592 | S | acetyl | " | 250–252 |
| 50 | 593 | S | propionyl | " | 224–226 |
| 51 | 594 | S | methylcarbamyl | " | 223–225 |
| 52 | 595 | S | ethylcarbamyl | " | 207–208 |
| 53 | 596 | S | propylcarbamyl | " | 218–220 |
| 54 | 597 | S | isopropyl-carbamyl | " | 214–215 |
| 55 | 598 | S | butylcarbamyl | " | 185–187 |
| 56 | 599 | S | tert.-butyl-carbamyl | " | 125–127 |
| 57 | 600 | S | phenylcarbamyl | " | 222–224 |
| 58 | 601 | S | hydrogen | 2,6-dichloro-3-methyl | 214–216 |
| 59 | 602 | S | acetyl | " | 238–240 |
| 60 | 603 | S | propionyl | " | 243–245 |
| 61 | 604 | S | ethylcarbamyl | " | 211 |
| 62 | 605 | S | propylcarbamyl | " | 185 |
| 63 | 606 | S | isopropyl-carbamyl | " | 201–203 |
| 64 | 607 | S | butylcarbamyl | " | 138–140 |
| 65 | 610 | S | phenylcarbamyl | 3-chloro | 123 |
| 66 | 611 | S | phenylcarbamyl | 3-trifluoro-methylphenyl | 180 |
| 67 | 612 | S | parachloro-phenylcarbamyl | " | 177–179 |
| 68 | 613 | S | hydrogen | 3-methyl | 162–164 |
| 69 | 614 | S | acetyl | " | 198–200 |
| 70 | 615 | S | propionyl | " | 206–209 |
| 71 | 616 | S | methylcarbamyl | " | 178 |
| 72 | 617 | S | ethylcarbamyl | " | 197 |
| 73 | 618 | S | propylcarbamyl | " | 192–193 |
| 74 | 619 | S | isopropyl-carbamyl | " | 182–183 |
| 75 | 620 | S | butylcarbamyl | " | 153 |
| 76 | 671 | S | hydrogen | 4-methyl | 164–170 |
| 77 | 672 | S | acetyl | " | 247–248 |
| 78 | 673 | S | propionyl | " | 214–215 |
| 79 | 674 | S | methylcarbamyl | " | 177 |
| 80 | 675 | S | ethylcarbamyl | " | 163 |
| 81 | 676 | S | propylcarbamyl | " | 202–204 |
| 82 | 677 | S | isorpopyl-carbamyl | " | 208 |
| 83 | 678 | S | butylcarbamyl | " | 188–190 |
| 84 | 679 | S | phenylcarbamyl | " | 152 |

We claim:

1. A compound of the following structure:

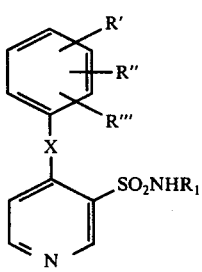
(I)

in which X represents an oxy or thio group; $R_1$ represents a group of the formula:

(II)

wherein $R_3$ represents a $C_1$–$C_4$-alkyl, cyclohexyl, unsubstituted phenyl or substituted phenyl group, or $R_1$ represents a group of the formula:

$$R_4 CO \qquad (III)$$

wherein $R_4$ represents a $C_1$–$C_4$-alkyl group or an unsubstituted or substituted phenyl group; R', R" and R''' represent each hydrogen or a substituent selected from the group comprising the halogen atoms, the trifluoromethyl group and the $C_1$–$C_4$-alkyl groups, as well as the pyridine N-oxide of the compounds of Formula I and the pharmaceutically acceptable base and acid addition salts of said compounds.

2. A compound according to claim 1, in which X is a thio group, $R_1$ is acetyl, propionyl, parachlorobenzoyl or a $R_3$-carbamyl group, and one of the symbols R', R" and R''' represent 3-methyl or one or two of the symbols R', R", and R''' represent chlorine, the other being hydrogen.

3. A compound according to claim 1, in which X is a thio group, $R_1$ is acetyl, propionyl, para-chlorobenzoyl or a $R_3$-carbamyl group, and one of the symbols R', R"

and R''' represent 3-trifluoromethyl or 4-methyl, the others being hydrogen.

4. 4-(3'-chlorophenoxy)-3-$R_3$-carbamylsulfonamidopyridines according to claim 1.

5. 4-(3'-trifluoromethylthiophenoxy)-3-alkylcarbamylsulfonamidopyridines.

6. Pharmaceutical compositions containing a hypouricemic or hypo-lipemic effective amount of at least one compound according to claim 1 as active ingredient, together with a pharmaceutical carrier or vehicle.

* * * * *